United States Patent [19]

Tetsuya et al.

[11] Patent Number: 4,542,005

[45] Date of Patent: Sep. 17, 1985

[54] PROCESS FOR PREPARING SILICON HYDRIDES

[75] Inventors: Iwao Tetsuya; Hirai Reiji; Ashida Yoshinori, all of Takaishi, Japan

[73] Assignee: Mitsui Toatsu Chemicals, Inc., Tokyo, Japan

[21] Appl. No.: 485,121

[22] PCT Filed: Jul. 6, 1982

[86] PCT No.: PCT/JP82/00254

§ 371 Date: Mar. 8, 1983

§ 102(e) Date: Mar. 8, 1983

[87] PCT Pub. No.: WO83/00140

PCT Pub. Date: Jan. 20, 1983

[30] Foreign Application Priority Data

Aug. 7, 1981 [JP] Japan .................................. 56-105706

[51] Int. Cl.$^4$ .............................................. C01B 33/04
[52] U.S. Cl. ...................................... 423/347; 556/474
[58] Field of Search ......................... 423/347; 556/474

[56] References Cited

U.S. PATENT DOCUMENTS 3,099,672 7/1963 Cooper et al. .
3,496,206 2/1970 Berger .................................. 556/474

FOREIGN PATENT DOCUMENTS 1049835 2/1959 Fed. Rep. of Germany .
57-209815 12/1982 Japan .................................. 423/347
781533 8/1957 United Kingdom ................ 556/474

*Primary Examiner*—Jack Cooper
*Attorney, Agent, or Firm*—Kane, Dalsimer, Kane, Sullivan and Kurucz

[57] ABSTRACT

In preparing of silicon hydrides with use of a mixture of an alkyl aluminum hydride and a trialkyl aluminum as a reducing agent for a silicon compound, an aluminum halide compound is added to said mixture in an amount sufficient for converting at least 90 mol % of the trialkyl aluminum to a dialkyl aluminum monohalide prior to the reduction reaction. Silicon hydrides are obtained with a high yield and quality.

1 Claim, No Drawings

PROCESS FOR PREPARING SILICON HYDRIDES

FIELD OF THE INVENTION

This invention relates to a process for the preparation of silicon hydrides, particularly monosilane, disilane and derivatives thereof with high yield and reduced amount of by-products.

BACKGROUND OF THE ART

It has been conventionally known to prepare monosilane, disilane or derivatives thereof by using an alkyl aluminum hydride. For example, in Japanese patent application Publication No. 36-517, British Pat. No. 823,483, German Pat. Nos. 1,055,511 and 1,117,090, there is disclosed a process for preparing a silicon hydride by the reduction of a silicon halide with sodium hydride in the presence of an alkyl aluminum hydride. In this known process, it is sodium hydride that serves as reducing agent for the silicon halide, and the alkyl aluminum hydride is added in such a small amount as 0.1–30% so that it serves only as an activating agent.

Another process for the reduction of a silicon halide is disclosed in French Pat. No. 1,499,032, in which the reducing agent consists of an alkyl aluminum hydride only.

These processes, however, are not yet satisfactory in that the yield of end products is lower and high quality is not obtained.

From the industrial standpoint, it is more advantageous to utilize an alkyl aluminum hydride in the form of a mixture of said alkyl aluminum hydride and a trialkyl aluminum rather than as pure alkyl aluminum hydride, since such a mixture is commercially available at a low price. However, when the reduction of a silicon halide is conducted using such a mixture of alkyl aluminum hydride and trialkyl aluminum, there is an extremely low yield of a silicon hydride, together with a large amount of by-produced silicon halide hydride, for example, monochlorosilane $SiH_3Cl$, which is probably produced because of insufficient reduction of the silicon halide. In addition, there is produced a large amount of ethane as by-product.

An object of the present invention is to provide a process for the preparation of silicon hydrides with improved yield and reduced amount of by-products without lowering the activity of alkyl aluminum hydride by using a mixture of an alkyl aluminum hydride and a trialkyl aluminum which is easily available as the reducing agent for silicon halides.

DISCLOSURE OF THE INVENTION

In accordance with the present invention there is provided a process for the preparation of silicon hydrides by reducing a silicon compound with a mixture of an alkyl aluminum hydride and a trialkyl aluminum, which comprises adding preliminarily into said mixture an aluminum halide compound in an amount sufficient for converting at least 90 mol percent of the trialkyl aluminum to a dialkyl aluminum monohalide prior to the reduction reaction.

Surprisingly, it has been found that when adding a specified amount of the aluminum halide compound to the mixture of alkyl aluminum hydride and trialkyl aluminum prior to the reduction of the silicon compound, silicon hydrides of high yield are obtained without reducing the activity of alkyl aluminum hydride and by-producing of silicon halide hydride and ethane is extremely reduced.

BEST MODE FOR CARRYING OUT THE INVENTION

The starting silicon compound which may be used in the present invention is a compound of the formula $Si_nX_{2n+2}$ in which n is an integer equal to or larger than 1 and the X's may be the same or different and represent halogen atoms, hydrogen atoms, alkoxy groups, alkyl groups, aryl groups or vinyl groups, the case of all X's being hydrogen atoms being excluded. The larger n becomes, the more difficult it is to handle such silicon compound and therefore to work the present invention.

Typical groups or atoms as X include methyl group, ethyl group, propyl group, n-butyl group, iso-butyl group, pentyl group, vinyl group, phenyl group, p-methylphenyl group, methoxy group, ethoxy group and halogen atoms such as chlorine and bromine. As the preferred compound falling within the above-mentioned general formula for use in the present invention there are included such compounds as silicon tetrachloride, hexachlorodisilane, tetraethoxysilane, diethyldichlorosilane or trichlorosilane.

The alkyl aluminum hydride for use in the present invention is a reducing compound having the general formula $R_2AlH$. The symbol R represents an alkyl group having 1 to 10 carbon atoms including ethyl group, n-propyl group or iso-butyl group. The preferred compounds expressed by said general formula include such compounds as diethyl aluminum hydride or diisobutyl aluminum hydride.

The trialkyl aluminum to be used in the present invention is a compound expressed by the general formula $R_3Al$. The symbol R represents an alkyl group having 1–10 carbon atoms, for example, ethyl group, n-propyl group or iso-butyl group. As preferred compounds of the formula, there can be exemplified such compounds as triethyl aluminum and tri-isobutyl aluminum.

It is often the case, with a mixture of an alkyl aluminum hydride and trialkyl aluminum, which is available commercially at a low price, that the alkyl groups of the alkyl aluminum hydride and the trialkyl aluminum are the same. However, for the process of the present invention, a mixture can be used in which the alkyl groups of the alkyl aluminum hydride and the trialkyl aluminum are different. The mixture of alkyl aluminum hydride and trialkyl aluminum is generally available in a proportion of 3:7 to 8:2 (by weight ratio).

The aluminum halide compound for use in the present invention is a compound expressed by the general formula $AlR_nX_{3-n}$. X represents halogen atoms such as chlorine or bromine. R represents alkyl groups having 1–10 carbon atoms such as ethyl group, n-propyl group or iso-butyl group. However, the presence of alkyl group is not always necessary, and thus, n is a number selected from 0, 1 and 1.5. As preferred compounds, there can be exemplified such compounds as ethyl aluminum dichloride, ethyl aluminum sesquichloride, iso-butyl aluminum dichloride or aluminum chloride. A mixture of such compounds can also be used in the present invention. The alkyl group of the alkyl aluminum halide to be added to the mixture of alkyl aluminum hydride and trialkyl aluminum may be the same as the alkyl groups of each component of said mixture. Otherwise, the alkyl groups of these three components may be different from one another.

The dialkyl aluminum monohalide formed from the conversion of the trialkyl aluminum may be expressed by the general formula $AlR_1R_2X$. $R_1$ and $R_2$ are the same or different and represent alkyl groups having 1 to 10 carbon atoms such as ethyl group, n-propyl group or iso-butyl group. X represents halogen atoms such as chlorine or bromine. As the compounds of the formula there can be exemplified such compounds as diethyl aluminum monochloride or di-isobutyl aluminum monochloride.

According to the present invention, the aluminum halide compound must be added to the mixture of alkyl aluminum hydride and trialkyl aluminum in such an amount as to convert at least 90 mol percent of the trialkyl aluminum to the dialkyl aluminum monohalide. This amount to be added is determined by the amount of trialkyl aluminum in the mixture and the amount of halogen atoms present in the aluminum halide compound. For example, in case of using alkyl aluminum dihalides or alkyl aluminum sesquihalides, these must be added in an amount of at least 90 mol % of the trialkyl aluminum present in the mixture. In case of aluminum chloride, this must be added in an amount of at least 45 mol % of the trialkyl aluminum.

According to the present invention, the aluminum halide compound is reacted with the trialkyl aluminum to form the dialkyl aluminum monohalide as shown hereunder:

$$R_3Al + AlRX_2 \rightarrow 2AlR_2X$$

$$R_3Al + Al_2R_3X_3 \rightarrow 3AlR_2X$$

$$2R_3Al + AlCl_3 \rightarrow 3AlR_2Cl$$

Namely, the alkyl aluminum dihalide or alkyl aluminum sesquihalide are reacted with the chemical equivalent of the trialkyl aluminum to form the dialkyl aluminum monohalide, while aluminum chloride is reacted with ½ equivalent of the trialkyl aluminum to form the dialkyl aluminum monohalide. For this reason the aluminum halide compounds must be added in the amount of at least 90 mol % or at least 45 mol %, respectively. The maximum amount of the aluminum halide compound to be added is not limited. However, even addition of such compound in a larger amount will provide no particular effects. Rather, too much addition of such compound is not preferred since it leads to the reduction of the concentration of said compound and an increase in the total volume of the reaction system, which result in commercial disadvantages such as decrease in the reaction velocity, increase in the required volume of the reaction vessel or increase in required heat supply.

The addition of the aluminum halide compound to the mixture of alkyl aluminum hydride and trialkyl aluminum may be accomplished by admixing the former directly with the latter. Otherwise, it may be done by diluting each component with a solvent and then admixing the resultants. In almost all cases, there will evolve heat due to admixing, and hence, care must be taken to avoid excessive heating. If one or more of the compounds to be admixed is solid, such compound may be dissolved in a solvent or suspended in a suitable medium, prior to the addition reaction. In the latter case where the compound is suspended, heating is preferable, in order to accelerate the reaction.

According to the present invention, a silicon hydride is produced by the reduction reaction of the silicon compound as herein defined with the mixture of alkyl aluminum hydride and trialkyl aluminum, which has been added with the aluminum halide compound, in the manner, for example, as expressed by the equation, $$SiCl_4 + 4Al(C_2H_5)_2H \rightarrow SiH_4 + 4Al(C_2H_5)_2Cl$$

or $$Si(OC_2H_5)_4 + 4Al(C_2H_5)_2H \rightarrow SiH_4 + 4Al(C_2H_5)_2(OC_2H_5)$$

Such reduction reaction may be carried out without any solvent. However, the use of a solvent is generally preferable for assuring that the reaction proceeds moderately. The solvent is preferably the one that will neither react with alkyl aluminum compounds present in the reaction system nor form aluminum complex, so that the alkyl aluminum compounds can be recovered after the reduction reaction. Preferable solvents are aliphatic hydrocarbons or aromatic hydrocarbons such as heptane, octane, liquid paraffin, benzene or toluene. A polar solvent, such as diethyl ether or tetrahydrofuran, may be used, if desired, to accelerate the reduction reaction at a lower temperature. However, such a polar solvent will form a complex salt with alkyl aluminum compounds, and hence, it is extremely difficult to separate and recover the alkyl aluminum compound from the reaction system. It is impossible to make such separation by means of such a simple procedure as distillation. It should be further noted that the use of a solvent such as carbon tetrachloride must be avoided, since it will react with alkyl aluminum compounds.

The reduction reaction will not proceed properly if the temperature is too low, while there will occur decomposition of the alkyl aluminum compounds and formation of side reactions at excessively high temperatures. Thus, the reduction reaction may be carried out generally in the range of $-30°$ C. to $100°$ C., more preferably in the range of $0°$ C. to $50°$ C. The reduction reaction will proceed sufficiently under a pressure in the range of atmospheric pressure to 2 Kg/cm² (gauge). However, the reaction may also be carried out under higher or lower pressures, depending upon the temperature or the reactor employed.

The reactants and the products of the reduction reaction are all active and, most of them will decompose or ignite by the reaction with oxygen or water. Thus, reaction must be conducted under an atmosphere where the reactants and the products are kept inactive with oxygen and water, for example, under the atmosphere of an inert gas (e.g. helium or argon), nitrogen or hydrogen which has been sufficiently removed of oxygen and water contents.

The reduction reaction may be carried out in any manner, i.e., batch-wise, semibatch-wise or continuously.

According to the process of the present invention, there can be obtained at a lower cost concurrently a silicon hydride and an alkyl aluminum monohalide in the following manner, which has been hitherto otherwise very expensive: An alkyl aluminum hydride, a trialkyl aluminum and an alkyl aluminum halide, which have the same alkyl groups, are subjected to the reduction reaction, in such a proportion that the amount of these alkyl groups to the amount of halogen atoms present in the silicon halide (as raw material) and alkyl aluminum halide be 2:1 by mol. Then, following the separation of a silicon hydride (the main product) from the reaction system, there can be very easily recovered from the remaining reaction system a single dialkyl aluminum monohalide, for example, by means of distillation.

According to the present invention, there is produced silicon hydride, such as monosilane, disilane, diethyldihydrosilane or the like. These silanes are of commercial importance since they have a variety of applications including uses as raw materials for synthesizing organic compounds or inorganic compounds, fuels or catalysts. The monosilane prepared by the process of the present invention contains minimal amount of impurities, and hence, through a simple refining procedure, serves as a raw material for various types of semiconductors.

The invention will be more fully described by reference to the following examples, but, the examples are not for restricting the scope of the invention.

EXAMPLE I

A stainless steel autoclave, having a volume of 500 ml and provided with an induction stirring device, was connected, via a gas flow meter, with a stainless steel vessel for trapping gas. The autoclave was also connected with a pump for feeding silicon tetrachloride dissolved in liquid paraffin therein. The whole system was filled with helium gas, prior to the reaction. The gas-trapping vessel was kept cool by means of liquid nitrogen.

A mixture (49.2 g) of 70% by weight of diethyl aluminum hydride and 30% by weight of triethyl aluminum was dissolved in 50 g of liquid paraffin. The amounts of the diethyl aluminum hydride and the triethyl aluminum were 0.4 mols and 0.129 mol, respectively. There was dissolved 16.4 g (0.129 mols) of ethyl aluminum dihalide in 23 g of liquid paraffin, and the resultant solution was added drop-wise to the above-mentioned mixture. As will be noted, the amount of the ethyl aluminum dichloride used is the one to convert the total mols of the triethyl aluminum to diethyl aluminum monochloride.

The mixture of the three alkyl aluminum compounds was placed in a vessel and maintained for 20 minutes at 30° C. under the pressure of 2 mmHg for degasification. Then, the mixture was placed into the autoclave under a helium atmosphere. Meanwhile, 17.0 g (0.1 mols) of silicon tetrachloride was dissolved in 28 g of liquid paraffin, and the resulting solution was forced, by means of the pump, into the autoclave, which was kept at 40° C., over a 2-hour period. The monosilane gas produced was caught in the trapping vessel. After the reaction was completed, the remaining monosilane was pressed out by helium to be caught in the trapping vessel.

The composition of the gas trapped was determined by means of gas chromatography. It was found that the production of the monosilane gas was 2.04 l (under normal condition) and the yield thereof was 91%. The ratio of ethane produced to the monosilane (ethane/SiH$_4$) and that of monochlorosilane to the monosilane (SiH$_3$Cl/SiH$_4$) were found to be 0.15% and 50 ppm, respectively.

COMPARATIVE EXAMPLE I

The same procedure as in Example I was repeated, except that ethyl aluminum dichloride was not added. The production and the yield of monosilane were 0.29 l (under normal condition) and 13%, respectively.

Ethane/SiH$_4$ and SiH$_3$Cl/SiH$_4$ were found to be 1.5% and 2.1%, respectively.

EXAMPLE II

The reduction of tetraethoxy silane was performed in the same procedure as in Example I with the same amounts of the alkyl aluminum compounds as in Example I, except that 70 ml of toluene, which had been sufficiently removed of water and oxygen, was used as a solvent, in place of the liquid paraffin, and that 20.8 g (0.1 mols) of tetraethoxy silane dissolved in 30 ml of toluene (removed of water and oxygen) was used in place of the silicon tetrachloride dissolved in the liquid paraffin. The period of the reaction was 1.3 hours, and the reaction temperature was 20° C.

The production of monosilane gas was 1.97 l (under normal condition) and the yield thereof was 88%. Ethane/SiH$_4$ was found to be 0.3%.

COMPARATIVE EXAMPLE II

The same procedure as in Example II was repeated, except that ethyl aluminum dichloride was not added. The production of monosilane was 1.1 l (under normal condition) and the yield of the same was 49%. Ethane/SiH$_4$ was found to be 1.1%.

EXAMPLE III

The reduction reaction was conducted with the same apparatus and the same materials as in Example I. There was placed in the autoclave 17.0 g of silicon tetrachloride dissolved in 28 g of liquid paraffin. To a mixture of 49.2 g of diethyl aluminum hydride and triethyl aluminum was added drop-wise 16.4 g of ethyl aluminum dichloride dissolved in 23 g of liquid paraffin. The mixture of the three aluminum-containing compounds, after having been degasified, was fed into the autoclave by the pump over a 2-hour period. The reaction temperature was 40° C.

The production and the yield of monosilane were 1.90 l (under normal condition) and 85%, respectively. It was found that ethane/SiH$_4$ was 0.18% and SiH$_3$Cl/SiH$_4$ was 1200 ppm.

EXAMPLE IV

A mixture (75.7 g) of 75% of diisobutyl aluminum hydride and 25% of triisobutyl aluminum was dissolved in 50 g of n-heptane which had been removed of water and oxygen. The amounts of the di-isobutyl aluminum hydride and the triisobutyl aluminum were 0.4 mols and 0.096 mols, respectively. To the mixture, there was added drop-wise 15.6 g (0.1 mols) of isobutyl aluminum dichloride dissolved in 20 g of n-heptane. The amount of the dichloride used corresponds to that for converting the 104% of the triisobutyl aluminum to diisobutyl aluminum monochloride. The mixture of the three alkyl aluminum compounds was placed in the autoclave (500 ml) under an atmosphere of helium. Meanwhile, there was provided 17.0 g (0.1 mols) of silicon tetrachloride dissolved in 30 g of n-heptane. The subsequent procedure was the same as in Example I.

The production of monosilane was found to be 2.00 l (normal condition) while the yield thereof was found to be 89%. The ratio of butane produced to the monosilane (butane/SiH$_4$) was 0.16% and SiH$_3$Cl/SiH$_4$ was 200 ppm.

EXAMPLE V

A mixture (49.2 g) of 75% by weight of diethyl aluminum hydride and 30% by weight of triethyl aluminum was diluted with 50 g of liquid paraffin. To the resultant mixture was added drop-wise 16.4 g of ethyl aluminum dichloride (which corresponds to the amount for converting all the triethyl aluminum to diethyl aluminum monochloride) dissolved in 23 g of liquid paraffin. The mixture of the three alkyl aluminum compounds was introduced in the autoclave of 500 ml kept under an atmosphere of helium. Then, 15.7 g of ethyl dichlorosilane dissolved in 30 g of liquid paraffin was added. The reaction was conducted at 40° C. for one hour. The liquid phase product was analyzed by means of gas chromatography, showing that the yield of diethyl silane was 95%.

EXAMPLES VI, VII, VIII AND COMPARATIVE EXAMPLES III, IV

The influence of the variation in the amount of ethyl aluminum dichloride on triethyl aluminum was studied when it was added to a mixture of diethyl aluminum hydride and triethyl aluminum.

The apparatus and the procedure used were the same as in Example I, except that the mixture was the one of 50% by weight of diethyl aluminum hydride and 50% by weight of triethyl aluminum.

The results were shown in Table I, in which the conditions for the experiments were also shown.

It can be seen from this Table that, for satisfactory results of the reduction reaction, ethyl aluminum dichloride should be added in such an amount as to convert at least 90 mol percent of triethyl aluminum to diethyl aluminum monochloride.

TABLE I

|  | $\dfrac{\text{AlC}_2\text{H}_5\text{Cl}_2 \text{ added}}{\text{Al(C}_2\text{H}_5)_3 \text{ in the mixture}}$ (molar ratio) | A* (molar %) | Yield of monosilane (%) | $\dfrac{\text{Ethane}}{\text{SiH}_4}$ (%) | $\dfrac{\text{SiH}_3\text{Cl}}{\text{SiH}_4}$ (ppm) |
|---|---|---|---|---|---|
| Comparative Example III | 0.5 | 50 | 17.5 | 3.25 | 18500 |
| Comparative Example IV | 0.7 | 70 | 35.5 | 0.43 | 1300 |
| Example VI | 0.9 | 90 | 89.5 | 0.13 | 65 |
| Example VII | 1.1 | 100 | 91.0 | 0.12 | 60 |
| Example VIII | 4.0 | 100 | 80.0 | 0.202 | 200 |

*A = $\dfrac{\text{The amount of Al(C}_2\text{H}_5)_3 \text{ converted to Al(C}_2\text{H}_5)\text{Cl by AlC}_2\text{H}_5\text{Cl}_2}{\text{The amount of Al(C}_2\text{H}_5)_3 \text{ in the mixture}} \times 100$ (molar %)

EXAMPLES IX, X AND COMPARATIVE EXAMPLES V, VI

The influence was studied of the amounts of aluminum chloride on triethyl aluminum when the reduction was carried out using a mixture of diethyl aluminum hydride and triethyl aluminum.

The apparatus used and the synthetic method were the same as in Example I, except that the mixture consisted of 50% by weight of diethyl aluminum hydride and 50% by weight of triethyl aluminum, and further that the reaction of aluminum chloride with said mixture was carried out at 70° C. by dissolving the reactants in liquid paraffin.

The results were shown in Table II, from which it can be seen that, for satisfactory results of the reduction reaction, aluminum chloride is necessary to be added in such an amount to convert 90 mol % or more of triethyl aluminum to diethyl aluminum monochloride.

TABLE II

|  | $\dfrac{\text{AlCl}_3 \text{ added}}{\text{Al(C}_2\text{H}_5)_3 \text{ in the mixture}}$ (molar ratio) | B* (molar %) | Yield of monosilane (%) | $\dfrac{\text{Ethane}}{\text{SiH}_4}$ (%) | $\dfrac{\text{SiH}_3\text{Cl}}{\text{SiH}_4}$ (ppm) |
|---|---|---|---|---|---|
| Comparative Example V | 0.10 | 20 | 15 | 1.7 | 19500 |
| Comparative Example VI | 0.30 | 60 | 27 | 0.6 | 1800 |
| Example IX | 0.45 | 90 | 89 | 0.25 | 20 |
| Example X | 0.60 | 100 | 91 | 0.24 | 25 |

*B = $\dfrac{\text{The amount of Al(C}_2\text{H}_5)_3 \text{ converted to Al(C}_2\text{H}_5)_2\text{Cl by AlCl}_3}{\text{The amount of Al(C}_2\text{H}_5)_3 \text{ in the mixture}} \times 100$ (molar %)

INDUSTRIAL APPLICABILITY

As described above, according to the process for the preparation of silicon hydrides by the present invention, end products of high quality are obtained with high yield without reducing the activity of alkyl aluminum hydride and the amount of by-products such as monochlorosilane and ethane is reduced. There is a great utility in that a mixture of an alkyl aluminum hydride and a trialkyl aluminum which is commercially available easily is used as the reducing agent for reduction of silicon halides.

We claim:

1. A process for the preparation of silicon hydrides by reducing a silicon compound of the formula, $Si_nX_{2n+2}$ in which n is an integer equal to or larger than 1 and the X's may be the same or different and represent halogen atoms, hydrogen atoms, alkoxy groups, alkyl groups, aryl groups or vinyl groups, the case of all X's being hydrogen atoms being excluded; with a mixture of an alkyl aluminum hydride and a trialkyl aluminum, said alkyl aluminum hydride having the formula $R_2AlH$ in which R is an alkyl group of 1–10 carbon atoms; said trialkyl aluminum having the formula $R_3Al$ in which R is an alkyl group of 1–10 carbon atoms; which comprises; adding to said mixture an aluminum halide compound of the formula, $AlR_nX_{3-n}$ in which n represents 0, 1, or 1.5, X represents halogen atoms, and R represents an alkyl group having 1–10 carbon atoms, in an amount sufficient to convert at least 90 mol percent of the trialkyl aluminum to a dialkyl aluminum monohalide prior to the reduction of said silicon compound.

* * * * *